United States Patent
Park et al.

(10) Patent No.: US 9,912,840 B2
(45) Date of Patent: Mar. 6, 2018

(54) APPARATUS AND METHOD FOR SAMPLING IMAGES

(71) Applicant: Samsung Electronics Co., Ltd., Suwon-si (KR)

(72) Inventors: Hyoung Min Park, Seoul (KR); Kyoung Gu Woo, Seoul (KR); Jung Hoe Kim, Seongnam-si (KR); Baek Hwan Cho, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 229 days.

(21) Appl. No.: 14/661,269

(22) Filed: Mar. 18, 2015

(65) Prior Publication Data
US 2015/0365566 A1 Dec. 17, 2015

(30) Foreign Application Priority Data
Jun. 16, 2014 (KR) .......................... 10-2014-0073148

(51) Int. Cl.
*H04N 7/18* (2006.01)
*H04N 5/04* (2006.01)
(Continued)

(52) U.S. Cl.
CPC ............... *H04N 5/04* (2013.01); *A61B 8/085* (2013.01); *A61B 8/14* (2013.01); *A61B 8/145* (2013.01);
(Continued)

(58) Field of Classification Search
CPC ......... G06T 7/0079; G06T 2207/30096; G06T 2207/10132; G06T 7/0065; G06T 7/0012;
(Continued)

(56) References Cited

U.S. PATENT DOCUMENTS

| 5,782,768 A | 7/1998 | Hashimoto et al. |
| 6,953,576 B2 | 10/2005 | Zeng et al. |

(Continued)

FOREIGN PATENT DOCUMENTS

| EP | 1152364 A2 * | 11/2001 | ............... A61B 8/06 |
| EP | 1152364 B1 * | 9/2007 | ............... A61B 8/06 |

(Continued)

OTHER PUBLICATIONS

Extended European Search Report dated Nov. 13, 2015 in counterpart European Application No. 15170932.6 (4 pages in English).
(Continued)

*Primary Examiner* — Sath V Perungavoor
*Assistant Examiner* — Peet Dhillon
(74) *Attorney, Agent, or Firm* — Jefferson IP Law, LLP

(57) ABSTRACT

Disclosed are an image sampling apparatus and method. The image sampling apparatus includes a probe angular velocity detector configured to detect an angular velocity of a probe representing a change in an angle of the probe at a surface of an object, an image segmenter configured to receive the angular velocity and an image captured by the probe, and to segment the image into sub-regions based on the angular velocity, and a differential sampler configured to sample the sub-regions with a different sampling rate based on a position of a sub-region.

21 Claims, 14 Drawing Sheets

(51) Int. Cl.
  *G06K 9/46* (2006.01)
  *G06K 9/52* (2006.01)
  *A61B 8/08* (2006.01)
  *A61B 8/14* (2006.01)
  *A61B 8/00* (2006.01)

(52) U.S. Cl.
  CPC ............ *A61B 8/4444* (2013.01); *A61B 8/483* (2013.01); *A61B 8/5215* (2013.01); *A61B 8/5292* (2013.01); *G06K 9/46* (2013.01); *G06K 9/52* (2013.01); *G06K 2009/4666* (2013.01)

(58) Field of Classification Search
  CPC .... G06K 2009/4666; G06K 9/46; G06K 9/52; A61B 8/085; A61B 8/145; A61B 8/5292; A61B 8/4444; A61B 8/483; A61B 8/5215; A61B 8/14; H04N 5/04
  See application file for complete search history.

(56) References Cited

U.S. PATENT DOCUMENTS

| | | | |
|---|---|---|---|
| 2006/0247525 A1* | 11/2006 | Huo | G06T 7/0012 600/437 |
| 2007/0232908 A1* | 10/2007 | Wang | A61B 8/08 600/437 |
| 2010/0130818 A1 | 5/2010 | Jung et al. | |
| 2012/0014578 A1 | 1/2012 | Karssemeijer et al. | |
| 2012/0071758 A1* | 3/2012 | Lachaine | A61B 8/085 600/439 |
| 2012/0099771 A1 | 4/2012 | Lao | |
| 2012/0165673 A1 | 6/2012 | Park | |
| 2012/0294502 A1 | 11/2012 | Chan et al. | |
| 2012/0323121 A1 | 12/2012 | Miller | |
| 2013/0109953 A1 | 5/2013 | Wehnes et al. | |
| 2013/0165788 A1* | 6/2013 | Osumi | A61B 8/4444 600/443 |

FOREIGN PATENT DOCUMENTS

| | | |
|---|---|---|
| JP | 2666353 B2 | 6/1997 |
| JP | 4584674 B2 | 9/2010 |
| JP | 2013-52195 A | 3/2013 |
| KR | 10-2002-0023446 A | 3/2002 |
| KR | 10-0876673 B1 | 1/2009 |
| KR | 10-2014-0070081 A | 6/2014 |

OTHER PUBLICATIONS

H. D. Cheng, Juan Shan, Wen Ju, Yanhui Guo, Ling Zhang: "Automated breast cancer detection and classification using ultrasound images: A survey" Pattern Recognition 43(1): pp. 299-317 (2010).

Wikipedia "Medical Ultrasonography" URL: http://ko.wikipedia.org/wiki/%EC%9D%98%EB%A3%8C_%EC%B4%88%EC%9D%8C%ED%8C%8C In Korean with English translation 24 pages (Accessed Mar. 4, 2015).

Yu-Len Huang, Dar-Ren, and Ya-Kuang Liu; "Breast Cancer Diagnosis Using Image Retrieval For Different Ultrasonic Systems"; pp. 2957-2960; 2004; Department of Computer Science and Information Engineering Tunghai University; Department of General Surgery China Medical College & Hospital; Taichung, Taiwan.

Kyung Hoon Hwang and Wonsick Choe et al.; Computer Aided Diagnosis (CAD) of Breast Mass on Ultrasonography and Scintimammography; pp. 1-6; Jul. 2005; Department of Nuclear Medicine, Gachon Medical School, Incheon, Korea; Department of Radiology, Seoul National University, College of Medicine, Seoul, Korea; CAD Impact, Inc. Seoul, Korea.

Yu-Len Huang; Sheng-Hsiung Lin and Dar-Ren Chen; "Computer-Aided Diagnosis Applied to 3-D US of Solid Breast Nodules by Using Principal Component Analysis and Image Retrieval"; pp. 1802-1805; Sep. 1-5, 2005; Department of Computer Science and Information Engineering, Tunghai University, Taichung, Taiwan; Department of General Surgery, Changhua Christian Hospital, Changhua, Taiwan.

\* cited by examiner

APPARATUS AND METHOD FOR SAMPLING IMAGES

CROSS-REFERENCE TO RELATED APPLICATION

This application claims the benefit under 35 U.S.C. § 119(a) of Korean Patent Application No. 10-2014-0073148, filed on Jun. 16, 2014, the entire disclosure of which is incorporated herein by reference for all purposes.

BACKGROUND

1. Field

The following description relates to technology for a computer aided diagnosis (CAD) of an ultrasound image and to technology for sampling an ultrasound image.

2. Description of Related Art

Computer aided diagnosis (CAD) of an ultrasound image represents technology to enable users, such as doctors, to diagnose a disease of a patient by extracting a region of interest in an ultrasound image and analyzing features of lesions. The CAD processing is provided to detect a lesion included in a capture image, and to this end, the entire region of an image may be subject to various image processing techniques, for example, feature pyramid generation and sliding window matching. There is a tradeoff between the time for image processing and the detection accuracy of lesions detected by image processing.

In the conventional real time CAD technology this tradeoff is balanced such that CAD processing is performed only on selected images rather than all of the captured images. Images subjected to the CAD processing are selected by sampling at equal time intervals such that the images equally include captured human body regions. However, when a probe for ultrasound image capturing changes a photography angle, a movement distance according to rotation of each region in a captured image may vary depending on the depth from the surface of a human body. If CAD processing is performed only on some images that are sampled at equal time intervals among all images photographed at different photography angles, a lesion located remotely from the surface of a human body is less likely to be sampled when compared to a lesion located adjacent to the surface, which in turn, means it is less likely to be detected by CAD.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, an apparatus for sampling images includes a probe angular velocity detector configured to detect an angular velocity of a probe representing a change in an angle of the probe at a surface of an object, an image segmenter configured to receive the angular velocity and an image captured by the probe, and to segment the image into sub-regions based on the angular velocity, and a differential sampler configured to sample the sub-regions with a different sampling rate based on a position of a sub-region.

The image may include a view inside the object taken from the surface of the object, and the image segmenter may be further configured to segment the image in a depth direction from the surface to the inside of the object.

The image segmenter may be further configured to segment the image in a width direction perpendicular to the depth direction.

A shape, a size, and a number of the segmented sub-regions, and the sampling rate of the differential sampler may be determined in advance.

A shape, a size and a number of the sub-regions segmented by the image segmenter and a sampling rate of the differential sampler may be determined based on the angular velocity.

A shape, a size and a number of the sub-regions and a sampling rate may be determined based on a selected sampling mode.

The sampling mode may be selected from sampling modes that are stored in advance, and each sampling mode of the sampling modes may be determined based on a position of a lesion expected to be included in the image and a probability of detecting the lesion.

The differential sampler may be further configured to sample the sub-regions with a higher sampling rate as a depth from the surface of the object increases.

The object may be a human body.

In another general aspect, there is provided a computer aided diagnosis (CAD) apparatus including a probe angular velocity detector configured to detect an angular velocity of a probe representing a change in an angle of the probe at a surface of an object, an image segmenter configured to receive the angular velocity and an image captured by the probe, and to segment the image into sub-regions based on the angular velocity, a differential sampler configured to sample the sub-regions with a different sampling rate based on a depth of a sub-region from the surface of the object, and a CAD processor configured to perform image processing to detect a lesion based on a sampling result of the differential sampler.

The differential sampler may be further configured to sample the sub-regions with a higher sampling rate as a depth from the surface of the object increases.

The probe angular velocity detector may include a sensor, and is configured to transmit the probe angular velocity detected by the sensor to the image segmenter.

In yet another general aspect, there is provided a method of sampling an image, the method including detecting an angular velocity of a probe representing a change in an angle of the probe at a surface of an object, receiving the angular velocity and an image captured by the probe, segmenting the image into sub-regions based on the angular velocity, and differentially sampling the sub-regions with a sampling rate that is determined depending on a position of a sub-region.

The segmenting of the image into the sub-regions may include segmenting the image in a depth direction from the surface to the inside of the object.

The segmenting of the image into the sub-regions may include segmenting the image in a width direction perpendicular to the depth direction.

A shape, a size and a number of the segmented sub-regions, and the sampling rate may be determined in advance.

A shape, a size and a number of the segmented sub-regions, and a sampling rate of the differential sampler may be determined based on the angular velocity.

A shape, a size, and a number of the segmented sub-regions, and a sampling rate may be determined based on a selected sampling mode.

The sampling mode is selected from sampling modes that may be stored in advance, and each sampling mode of the plurality of sampling modes may be determined based on a position of a lesion expected to be included in the image and a probability of detecting the lesion.

The differential sampling of the sub-regions comprises sampling the sub-regions with a higher sampling rate as a depth from the surface of the object increases.

In yet another general aspect, there is provided a method of sampling an image, the method including detecting an angular velocity of a probe representing a change in an angle of the probe at a surface of an object, segmenting an image into sub-regions in a direction perpendicular to the surface of the object, in response to the angular velocity being greater than a first threshold, and differentially sampling the sub-regions with a sampling rate that is determined based on a position of a sub-region from the surface of the object.

The differential sampling of the sub-regions may include differentially sampling the sub-regions based on a selected sampling mode and a depth of the sub-region from the surface of the object.

The segmenting of the image into the sub-regions may include segmenting the image in a depth direction perpendicular to the surface of the object and in a width direction perpendicular to the depth direction, in response to the angular velocity being greater than a second threshold.

Other features and aspects will be apparent from the following detailed description, the drawings, and the claims.

Figure 1:
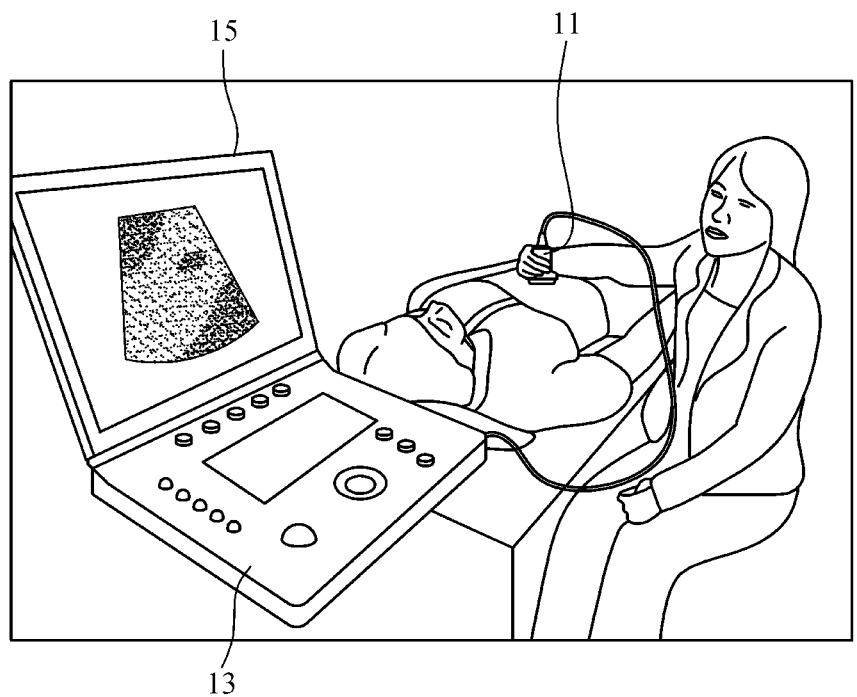
FIG. 1 is a schematic diagram illustrating an example of a general real-time CAD environment.

Throughout the drawings and the detailed description, unless otherwise described, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses, and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

FIG. 1 is a diagram illustrating a real-time CAD environment 10 to which an image sampling technology may be applied. In the real-time CAD environment 10, a user captures an image of a patient by using a probe for ultrasound image capturing 11. The probe 11 may capture an image by radiating an ultrasound signal to the inside of a human body, and receiving a reflected signal. The captured image is transmitted to a computing device 13 configured to perform a CAD process, and is subjected to CAD processing. Thereafter, a lesion detected by the CAD process is displayed through a display 15 of the computing device 13 while being overlaid on the captured image.

In general, ultrasound images captured by the probe 11 are captured at a rate of about 30 to 60 images per second. For the real-time CAD, a point of time for capturing an ultrasound image is required to match a point of time for finishing CAD processing. However, the ultrasound image has low resolution, and in order to enhance the accuracy of detecting lesions, the CAD processing accuracy needs to be increased, thereby leading to the processing time being increased. On the contrary, if the processing time is decreased, the accuracy of detecting lesion may be lowered. In order to improve the tradeoff between the time required for CAD process and the detection accuracy, a CAD process is performed on some images selected from all captured images.

Figure 2:
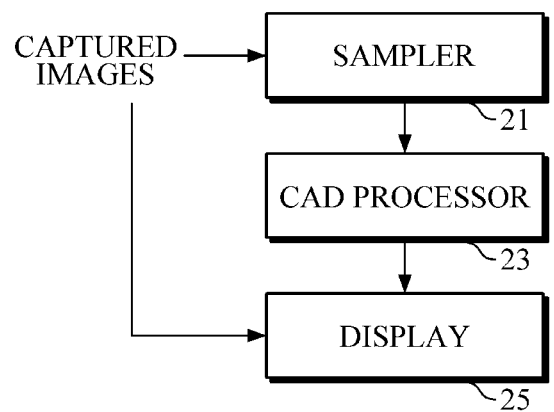
FIG. 2 is a diagram illustrating an example of a configuration of a apparatus for performing a real-time CAD according to the conventional technology.
Figure 3:
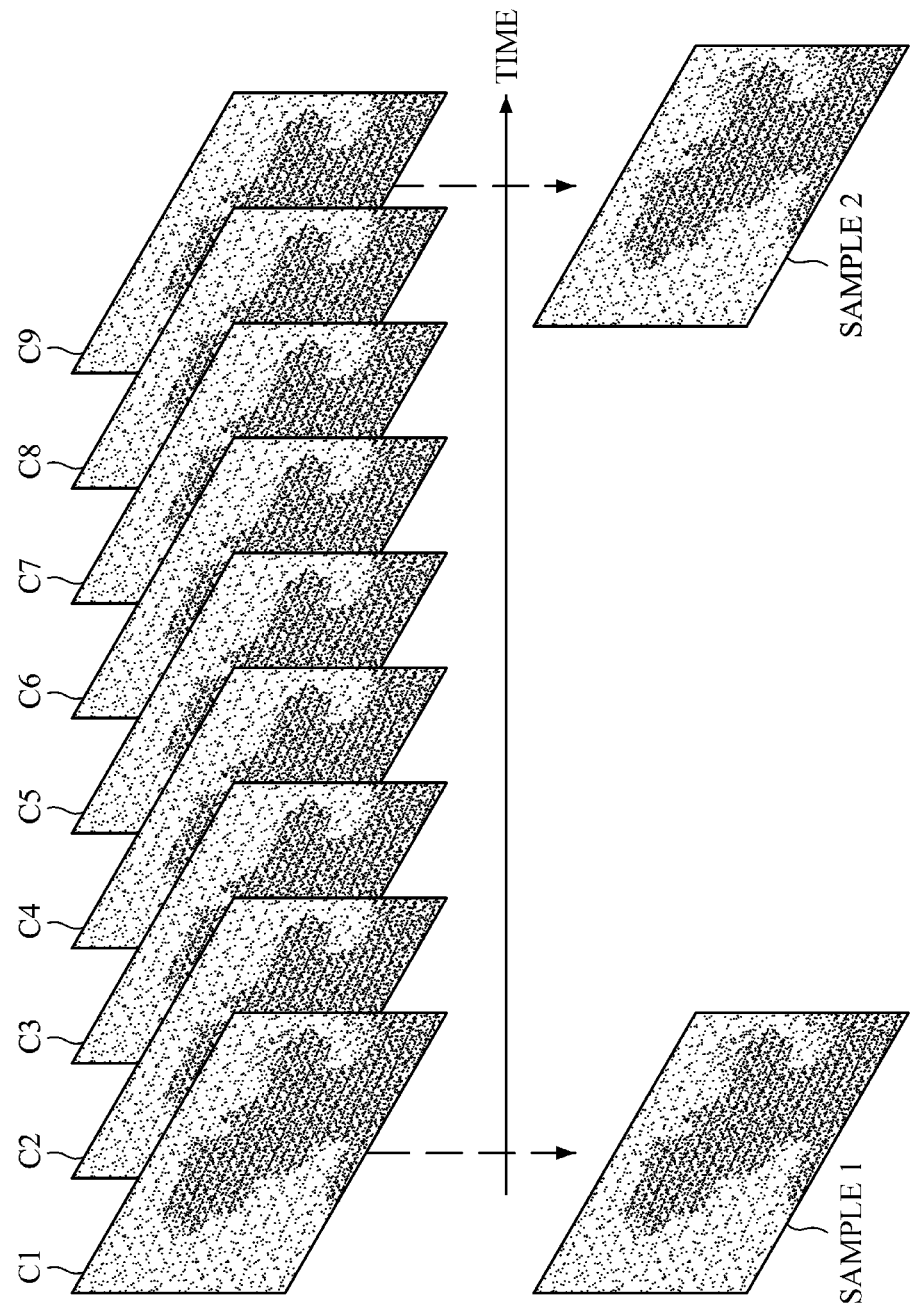
FIG. 3 is a diagram illustrating an example of an image sampling process of a real-time CAD according to the conventional technology.

FIGS. 2 and 3 illustrate a schematic configuration of a conventional real-time CAD apparatus 20 and a process of selecting an image that is to be processed by the apparatus 20. Referring to FIG. 2, a real-time CAD apparatus 20 may include a sampler 21, a CAD processor 23 and a display 25. The sampler 21 selects some of a plurality of captured images. Referring to FIG. 3, the sampler 21 may select some images (sample 1 and sample 2) among a plurality of captured images (C1 to C9) at predetermined time intervals one at a time. Although one image is selected from eight images in FIG. 3, such a description is provided only as an example of sampling at a predetermined time interval, and the sampling time interval may be varied. For example, when thirty images per second are captured by a probe, and it takes two seconds to perform a CAD process on a single image, the sampler 21 may select one image among sixty captured images as a sample, to implement a real-time CAD.

The CAD processor 23 may perform a CAD process (for example, a sliding window method) on the samples selected by the sampler 21. The result of the CAD process may be displayed through the display 25.

An image sampling apparatus and an image sampling method will be described with reference to FIGS. 4 to 13. The description of the image sampling apparatus and the image sampling method is for an illustrative purpose only, and those skilled in the art will appreciate that implementation of other apparatus and methods are considered to be well within the scope of the present disclosure. Although the image sampling apparatus and the image sampling method are illustrated as being used in real-time CADs, it may be used for other apparatuss, such as, for example, general CADs, without departing from the scope of the present disclosure.

Figure 4:
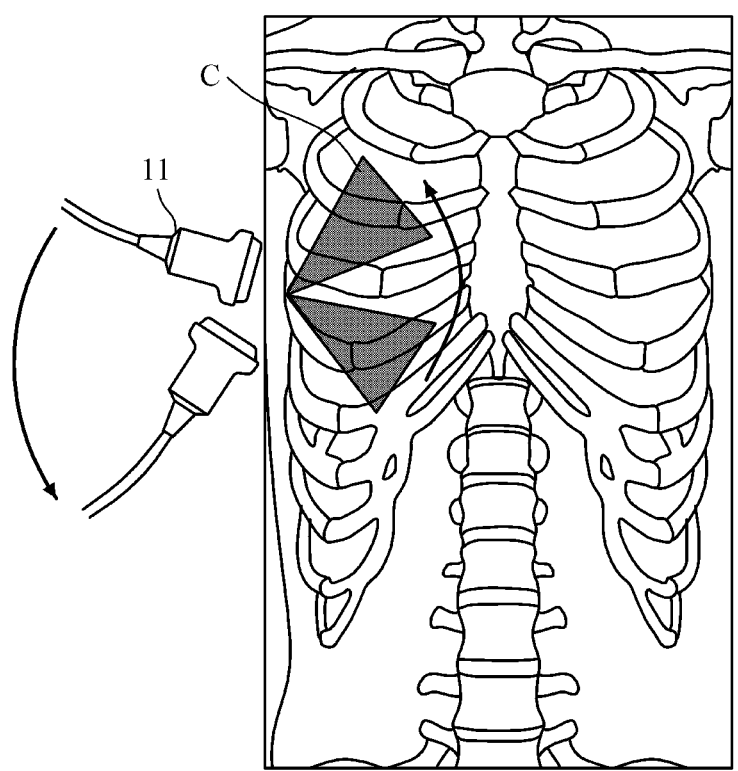
FIG. 4 is a diagram illustrating an example of a change in photography angles of an ultrasound image capturing probe when an ultrasound imaging is performed on an intercostal section.

FIG. 4 is a diagram illustrating an example of a change in photography angles of an ultrasound image capturing probe during an intercostal ultrasound imaging. Referring to FIG. 4, when an ultrasound image C captures internal organs of a human body through the ribs of a human, a user may photograph the inside of the human body while changing a probe angle within a predetermined range. The probe 11 photographs the inside of the human body through a fixed point on a surface of the human body, and ultrasound images C including different human body regions may be obtained depending on the angle of the probe 11. When a probe is moved by a predetermined angle, a region adjacent to the surface of the human body may be moved by a distance shorter than a distance moved by a region distant from the surface of the human body in the captured ultrasound images.

Figure 5:
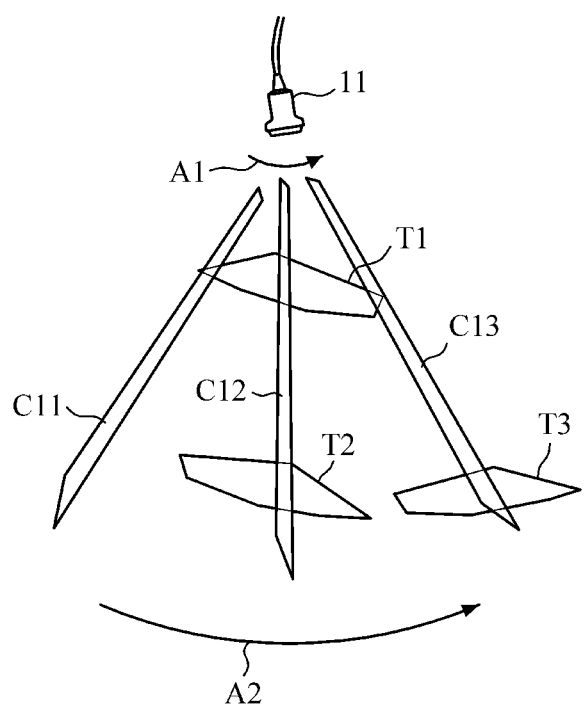
FIG. 5 is a diagram illustrating an example of a relation between captured images at different probe angles and lesions when a photography angle of an ultrasound image capturing probe is changed.

FIG. 5 is a diagram illustrating an example of a relation between captured images at different probe angles and lesions when a photography angle of an ultrasound image capturing probe is changed. Referring to FIG. 5, when the probe 11 changes an angle thereof in a direction of arrow A1, a region subjected to ultrasound imaging by the probe 11 is also changed at an angle thereof in the same direction as A1, so that image C11, image C12 and image C13 are sequentially captured. When inside regions of image C11 and image C13 are compared, a region adjacent to the surface of the human body has a movement distance as short as arrow A1, but a region distant from the surface of the human body has a movement distance as long as arrow A2. In FIG. 5, it may be assumed that a lesion T1 exists adjacent to the surface of the human body, and lesions T2 and T3 exist deep inside the human body. In this example, image C11 only includes T1, C12 includes T1 and T2, and C13 includes T3. If some images are sampled from among captured images as described in FIGS. 2 and 3 and only the images C11 and C13 are selected, the lesion T2 included in the omitted C12 may be not detected.

As such, as shown in FIG. 3, if a uniform sampling scheme of sampling images at equal time intervals is applied when a probe detects different images based on probe angles while changing the probe angles, the detection rate of a lesion located at a distance from the surface of the human body may be significantly lowered. Accordingly, in order to improve the detection accuracy of lesions, the sampling needs to be performed considering that movement distances of images that differ with the depth in the human body. To this end, the image sampling scheme according to present disclosure adopts a scheme of dividing an image into a plurality of sub-regions, and performing differential sampling based on the position of each sub-region in the image.

Figure 6A:
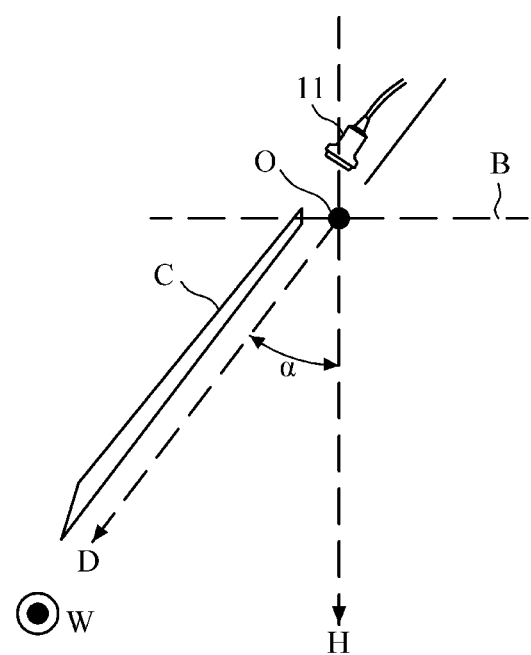
FIGS. 6A-6B are another diagrams illustrating an example of a relation between captured images and lesions according to a probe angle when a photography angle of an ultrasound image capturing probe is changed.
Figure 6B:
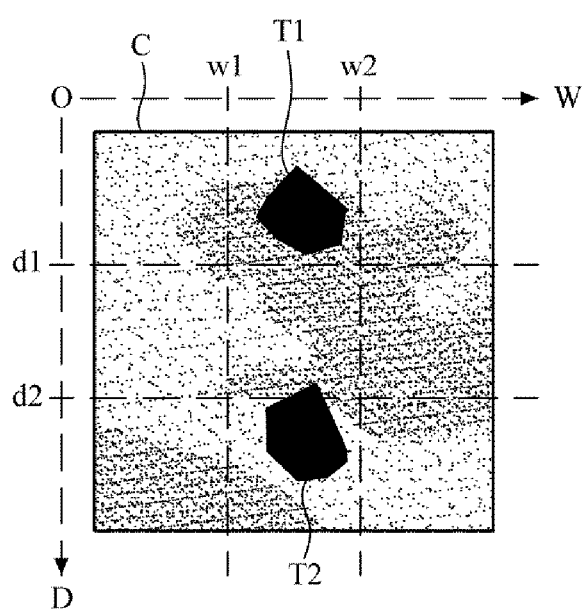

FIGS. 6A-6B are other diagrams illustrating examples of relation between captured images and lesions according to a probe angle when a photography angle of an ultrasound image capturing probe is changed. FIG. 6A illustrates a case in which an ultrasound image C is captured when the probe 11 inclines by an angle of a with respect to a vertical axis H at a point 0 on a surface of a human body B. The image C is a two dimensional ultrasound image, and shows a section in a direction D corresponding to a direction of the probe 11. A direction W denoted by the symbol ⊙ representing a head of an arrow indicates a direction oriented from a tail of arrow to a head of arrow.

FIG. 6B is a view rotated from FIG. 6A sideways by an angle of 90 degrees, and in which a depth direction D and a width direction W of an image C are shown. FIG. 6B illustrates an example in which the image C includes a lesion T1 adjacent to a surface of a human body and a lesion T2 distant from the surface of the human body. When the image C is divided based on lines d1 and d2 in the depth direction D, the image C is divided into three parts each including a sub-region (including an upper portion ranging from 0 to d1, a middle portion ranging from d1 to d2 and a lower portion ranging from d2 and below). FIG. 6B illustrates that the lesion T1 exists in the upper portion, and the lesion T2 exists in the lower portion.

For example, as shown in FIG. 6B, when the image C is divided based on lines d1 and d2 in the depth direction D and lines w1 and w2 in the width direction W, the image C is divided into nine parts, each including a sub-region.

When ultrasound images are captured while changing the probe angle, image at upper portions, which are adjacent to the surface of the human body have different photographic densities from image at lower portions, which are distant from the surface of the human body. The image at the upper portions are moved a short distance between a plurality of images, and correspond to a high density photography result in which photography is densely performed on a narrow region during the same period of time. Meanwhile, the image at the lower portions are moved a long distance between a plurality of images, and correspond to a low density photography result in which photography is sparsely performed on a wide region during the same period of time. By allowing the upper portion of the image to have a different sampling rate from that of the lower portion, a CAD process result is produced in consideration of a high density photography result and a low density photography result, and thus the detection accuracy of lesion is improved.

Conventional real-time CAD sampling scheme adopts an image unit selection scheme in which some images are selected among captured images, whereas the sampling scheme according to the present disclosure adopts a sub-region unit selection scheme in which some sub-regions are selected among sub-regions in each image, which produces a difference between the conventional sampling scheme and the sampling scheme according to the present disclosure.

In addition, the sampling scheme according to the present disclosure may apply a sampling rate that varies depending on a magnitude of an angular velocity of a probe. Continuous images captured with a low angular velocity correspond to a case of densely photographing a narrower region when compared to continuous images captured with a high angular velocity.

In addition, the sampling scheme according to the present disclosure may provide a sampling mode selectable by a user. For example, a user may desire to diagnose a lesion that is likely to be detected at a position adjacent to the surface of the human body. In another example, a user may desire to diagnose a lesion that is likely to be detected at a position distant from the surface of the human body. In yet another example, a user may desire to diagnose a region having almost no possibility of a lesion being detected or a region having a high possibility of a lesion being detected.

When a doctor performs ultrasound imaging to diagnose breast cancer, the doctor may photograph a region having almost no possibility of a lesion, such as a tumor of being detected. In this case, the doctor may perform ultrasound imaging with a passive intention to confirm that a lesion does not exist. To this end, the doctor may photograph at a low photography density by rapidly changing the probe. When a doctor photographs a region having a high possibility of a lesion being detected, the doctor may perform ultrasound imaging with an active intention to find a lesion. In this case, the doctor may photograph at a high photography density by slowly changing the probe.

As described above, a user may perform ultrasound imaging with a certain intention, and in order to reflect the intention, a plurality of sampling modes may be defined in advance based on incidence rates and occurrence positions of lesions. A user may select a proper sampling mode among the plurality of sampling modes before/during the ultrasound imaging using a probe. A method of dividing a captured image, a sampling rate depending on a position of a sub-region of a captured image, and a sampling rate depending on similarity may be determined corresponding to each sampling mode.

Figure 7:
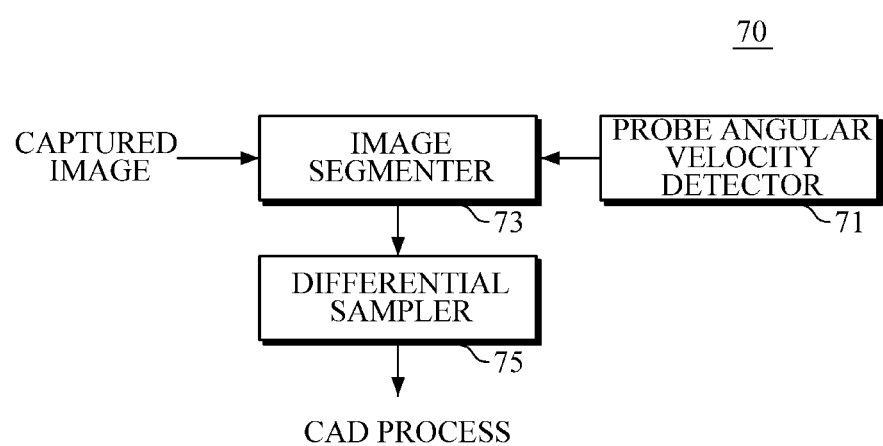
FIG. 7 is a diagram illustrating an example of a configuration of an image sampling apparatus.

FIG. 7 is a diagram illustrating an example of a configuration of an image sampling apparatus 70. Referring to FIG. 7, the image sampling apparatus 70 includes a probe angular velocity detector 71, an image segmenter 73 and a differential sampler 75.

The probe angular velocity detector 71 detects an angular velocity of a probe. The probe angular velocity detector 71 may detect an angular velocity through sensor devices, such as, for example, an accelerometer and a gyroscope, provided inside the probe, or through sensors installed outside the probe. The angular velocity represents a change in angle according to time. Accordingly, angular velocities provided by the probe angular velocity detector 71 may include values of probe angles detected at a predetermined point of time. The probe angles may represent a degree of inclination (for example, α in FIG. 6A) of an orientation of an image (for example, an image at depth direction D in FIG. 6A) captured by a probe with respect to a predetermined reference axis (for example, a vertical axis H in FIG. 6A).

The image segmenter 73 divides the image captured by the probe into a plurality of sub-regions. The image segmenter 73 may divide the image in a depth direction (for example, D in FIGS. 6A-6B). Alternatively, the image segmenter 73 may divide the image not only in a depth direction D but also in a width direction (for example, W in FIGS. 6A-6B). Such a method of dividing an image in the image segmenter 73 may be determined in advance. In another example, the method of dividing an image in the image segmenter 73 may be determined depending on a magnitude of an angular velocity provided by the probe angular velocity detector 71.

The differential sampler 75 selects one or more sub-region(s) among sub-regions of an image, which are divided by the image segmenter 73. The sub-region selected by the differential sampler 75 may be provided to a CAD process. The differential sampler 75 may determine whether to select a sub-region, based on a position of the sub-region in an image. For example, a sub-region located at a lower portion of an image (i.e., a portion distant from the surface of the human body) may be selected at a higher sampling rate when compared to a sub-region located at an upper portion of an image (i.e., a portion adjacent to the surface of the human body).

Therefore, when a probe captures an image while changing an angle of the probe, the region adjacent to the surface of the human body and the region distant from the surface of the human body may be sampled at an equal rate. In addition, only a part of the entire area of the capture image is sampled, thereby reducing the burden of the CAD process to be performed later. Accordingly, the present disclosure provides a real-time CAD scheme capable of preventing degradation of detection rates of lesions while performing a sufficient amount of samplings for a real-time CAD when an intercostal ultrasound image is performed on internal organs located at an inner side of ribs while changing a probe angle.

Figure 8:
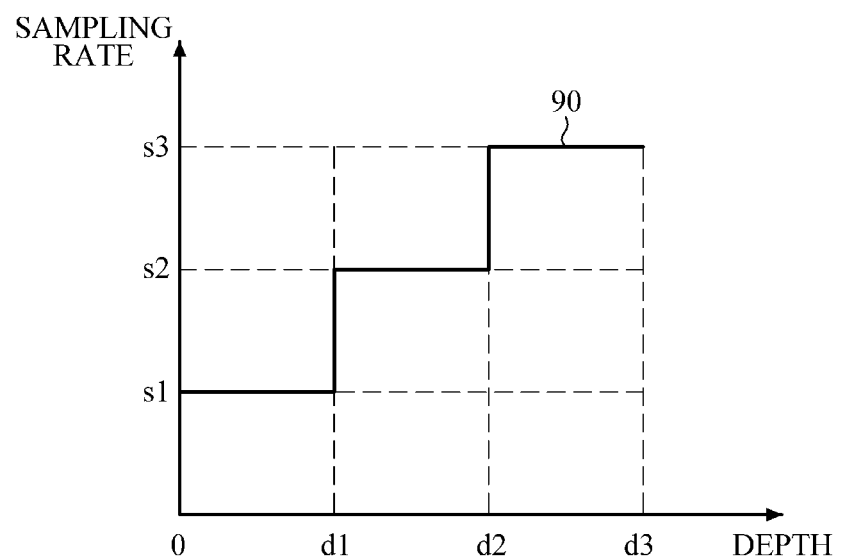
FIG. 8 is a diagram illustrating an example of a relation between a depth of an image and a sampling rate in the image sampling apparatus of FIG. 7.

FIG. 8 is a diagram illustrating an example of a relation between a depth of an image and a sampling rate in the image sampling apparatus of FIG. 7. In FIG. 8, a graph 90 shows an example in which the sampling rate is increased as a depth is increased. Here, the depth represents a degree by which the position of a sub-region is spaced apart from a surface of a human body that makes contact with a probe. In the graph 90, a position of 0 represents the surface of the human body making contact with the probe, and a greater depth (i.e., in the order of d3, d2 and d1) represents a position spaced further away from the surface of the human body. It should be understood that the depth does not represent a direction oriented from the entire area of the surface of the human body to the inside of the human body, but oriented from a point at which the probe makes contact with the surface of the human body. For example, when a surface of a human body making contact with a probe is a chest, a greatest depth value of d3 in the graph 90 may represent a surface at an opposite side of the human body, i.e., the back of the human body.

Referring to FIG. 8, the sampling rate is represented as s1, s2, and s3, which means that an image is divided into three sub-regions at the depths d1 and d2. In FIG. 8, the relation of the sampling rate and the depth is for an illustrative purpose only, and various relations between the sampling rate and the depth may be possible. For example, the image may be divided by the number of pixels in the depth direction, and in this case, the graph 90 may be provided in a substantially straight line.

Figure 9:
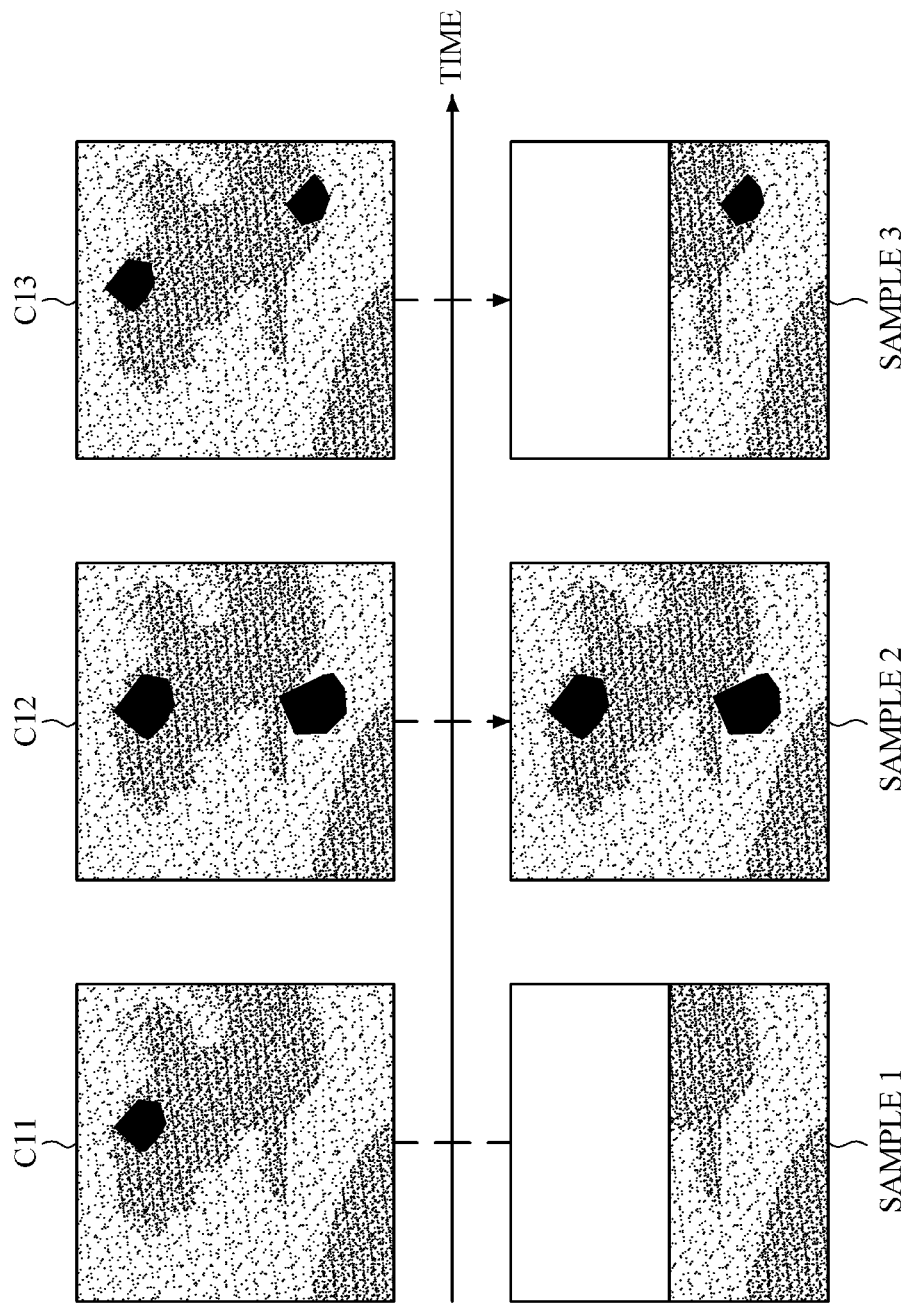
FIG. 9 is a diagram illustrating an example of a sampling result obtained by the image sampling apparatus of FIG. 7.

FIG. 9 is a diagram illustrating an example of a sampling result obtained by the image sampling apparatus of FIG. 7. Referring to FIG. 9, captured images C11, C12, and C13 are shown above a time axis. The images are different images obtained when a probe changes an angle at a position on a surface of a human body as described in FIG. 5. The sampling results of the image sampling apparatus 70 described in FIG. 7 are illustrated below the time axis. In this case, a lower portion of a captured image has a sampling rate higher than that of an upper portion of the image. For example, the lower portion has a sampling rate in which one lower portion is selected from each image, and the upper portion has a sampling rate in which one upper portion is selected from two images.

In this example, with respect to the three captured images C11, C12 and C13, one of two upper portions is selected and all lower portions are selected, producing the results of sample 1, sample 2 and sample 3. Referring to FIG. 9, a sampling is performed on the capture image C11, and as a result, sample 1 is output. Sample 1 shows that only the lower portion of the image C11 is selected. Meanwhile, sample 2 output as a result of sampling the captured image C12 is the same as the image C12. Sample 3 output as a result of sampling the captured image C13 shows that only the lower portion of the image C13 is selected. Thereafter, sample 1, sample 2, and sample 3 are provided to the real-time CAD for processing to detect lesions.

Figure 10:
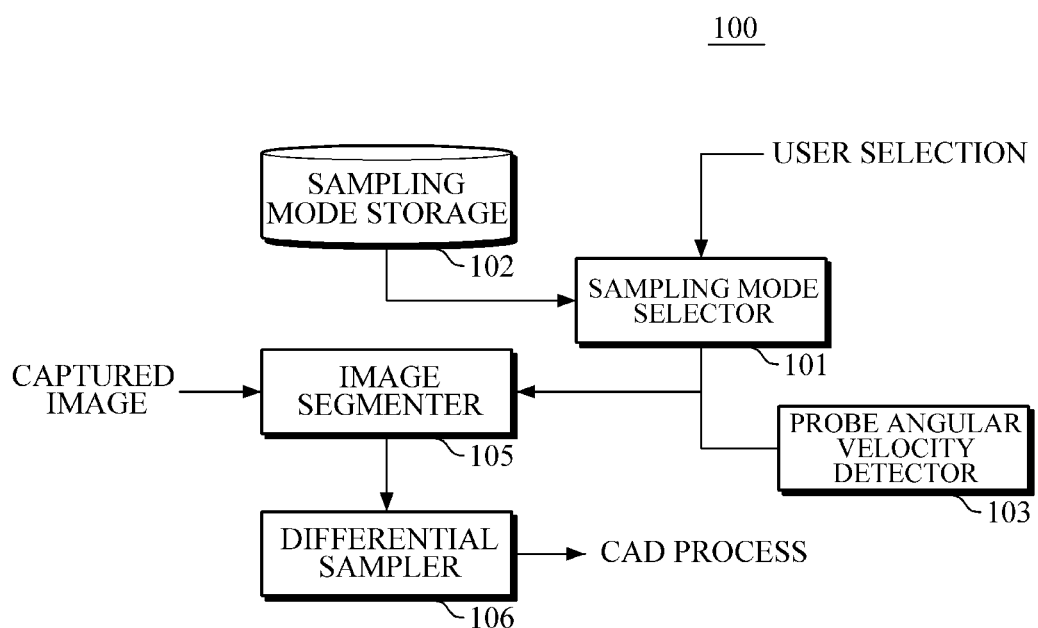
FIG. 10 is a diagram illustrating an example of a configuration of an image sampling apparatus.

FIG. 10 is a diagram illustrating an example of a configuration of an image sampling apparatus 100. Referring to FIG. 10, the image sampling apparatus 100 includes a sampling mode selector 101, a sampling mode storage 102, a probe angular velocity detector 103, an image segmenter 105, and a differential sampler 106.

The sampling mode selector 101 and the sampling mode storage 102 store predetermined sampling modes and permit a user to select a stored sampling mode. The sampling mode storage 102 may store predetermined sampling modes, such as, for example, a first mode, a second mode, and a third mode. The sampling mode may have sampling related parameters set in advance, for example, the sampling related parameter may include a method of dividing an image, the size and position of divided sub-regions, a sampling rate depending on the position, and a plan to compare a similarity with a previous image. The sampling mode may be determined in advance, to have predetermined parameters depending on a detection probability of a lesion desired for diagnosis and a position of a lesion to be detected.

The sampling mode selector 101 displays the sampling modes stored in the sampling mode storage 102 to a user. The sampling mode selector 101 also provides the user with a user interface to select one of the sampling modes. The user may select a desired sampling mode through the sampling mode selector 101. Sampling is performed on sub-regions of an image, according to the sampling mode selected by the user.

The probe angular velocity detector 103 corresponds to the probe angular velocity detector 71 described with reference to FIG. 7.

The image segmenter 105 divides an image captured by the probe into a plurality of sub-regions. The image segmenter 105 may divide the image in a depth direction D, or divide the image not only in a depth direction D but also in a width direction W. The method of dividing the image in the image segmenter 105 may be determined by a sampling mode selected by a user through the sampling mode selector 101. In another example, the method of dividing the image in the image segmenter 105 may be determined depending on a magnitude of an angular velocity provided by the probe angular velocity detector 103 as well as a sampling mode selected by a user.

The differential sampler 106 selects one or more sub-region(s) among sub-regions of an image, which are divided by the image segmenter 105. The sub-region selected by the differential sampler 106 may be directly provided to a CAD process. The differential sampler 106 may sample a sub-region at a different sampling rate depending on a position of the sub-region in an image. For example, a sub-region located at a lower portion of an image (that is, a portion distant from the surface of the human body) may be sampled at a higher sampling rate when compared to a sub-region located at an upper portion of an image (that is, a portion adjacent to the surface of the human body).

When a user captures an ultrasound image by using a probe, and performs a real-time CAD, a desired sampling mode is selected and input by the user. The image sampling apparatus 100 divides and samples the captured images according to a method determined by the detected probe angular velocity and the selected sampling mode, and the image sampling apparatus provides the CAD process with the result of sampling.

Figure 11:
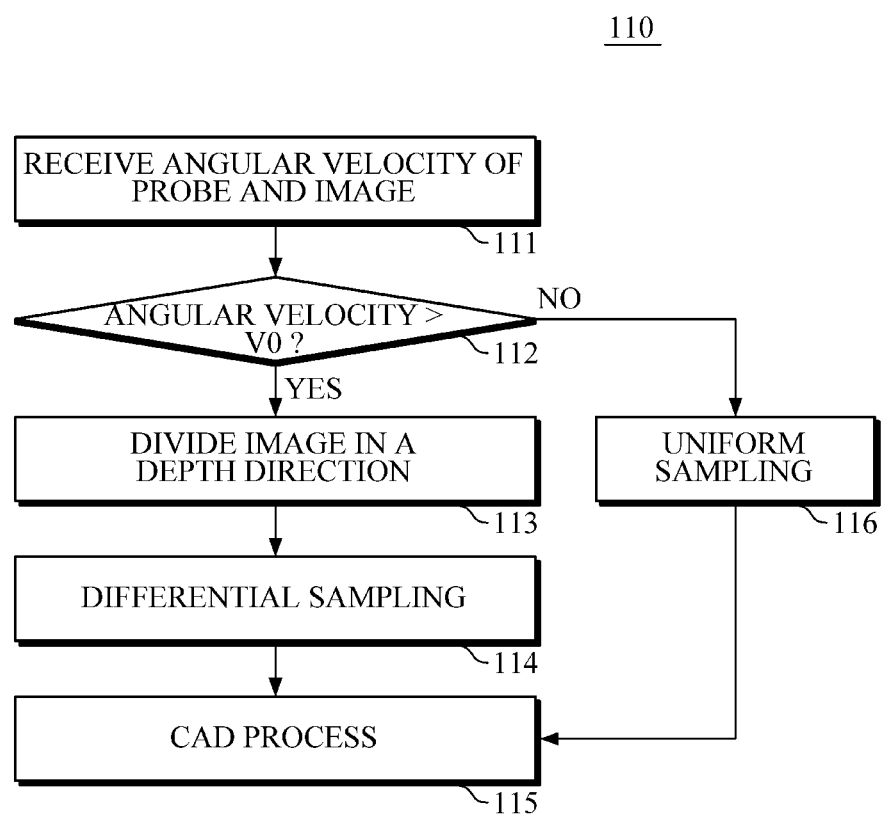
FIG. 11 is a diagram illustrating an example of an image sampling method.

FIG. 11 is a diagram illustrating an example of an image sampling method (110). Referring to FIG. 11, the image sampling method (110) represents a process of dividing a captured image in a depth direction according to a detected probe angular velocity, and performing differential sampling based on a depth. The operations in FIG. 11 may be performed in the sequence and manner as shown, although the order of some operations may be changed or some of the operations omitted without departing from the spirit and scope of the illustrative examples described. Many of the operations shown in FIG. 11 may be performed in parallel or concurrently. The above descriptions of FIGS. 1-10, is also applicable to FIG. 11, and is incorporated herein by reference. Thus, the above description may not be repeated here.

According to the image sampling method (110), in 111, an angular velocity of a probe capturing an ultrasound image is detected and a captured image is received. In 112, it is checked whether a magnitude of the detected angular velocity exceeds a predetermined threshold value V0.

The probe angular velocity may be detected when a probe changes an angle based on a point at which the probe makes contact with a surface of a human body. The angular velocity of the probe may represent a change in an inclination angle (for example, α in FIG. 6A) of a direction of an image captured by the probe (for example, a depth direction D of a human body in FIG. 6A), with respect to an axis perpendicular to a surface of a human body (for example, the vertical axis H in FIG. 6A) according to time.

If the magnitude of the probe angular velocity does not exceed a threshold value (i.e., NO is returned from operation 112), it is determined that there is no need to perform sampling in consideration of a change in the probe angle. The probe does not change an angle, and thus, in 116, uniform sampling is performed. As described in FIG. 3, the uniform sampling represents a method in which a single image is selected at uniform time intervals from captured images.

If the magnitude of the probe angular velocity exceeds a threshold value (i.e., YES is returned from operation 112), it is determined that there is a need to perform sampling in consideration of a change in the probe angle. A distance moved between adjacent capture images due to a change in the probe angle is increased with an increase of depth, and it is determined that there is a need of sampling in consideration of the increase of movement distance. In 113, the captured image is divided in a depth direction for the sampling.

In 113, the dividing of the captured image is a process of dividing each of the images captured by the probe into a plurality of sub-regions. In this process, each image may be divided into a plurality of sub-regions along a depth direction D as shown in FIG. 6B. In this example, the shape and size of each sub-region generated through the division may vary. For example, sub-regions may be divided to have the same shape and the same area. In another example example, sub-regions may be differentially divided to have a larger area with distance along the depth direction in an image. According to an embodiment, the sub-region dividing method in terms of the shape and area may be determined in advance regardless of the magnitude of the probe angular velocity.

In 114, differential sampling is performed. In 114, with respect to each image, one or more some sub region(s) may be selected among sub-regions divided in 113. In 115, the selected one or more some sub region(s) may be provided to the CAD process.

In the differential sampling (114), the criterion for selecting a sub-region may be determined based on a position of the sub region. For example, a sub-region of an image located distant in the depth direction D (that is, a lower portion of the image) may be selected at a higher sampling rate when compared to a sub-region located adjacent in the depth direction (that is, an upper portion).

Figure 12:
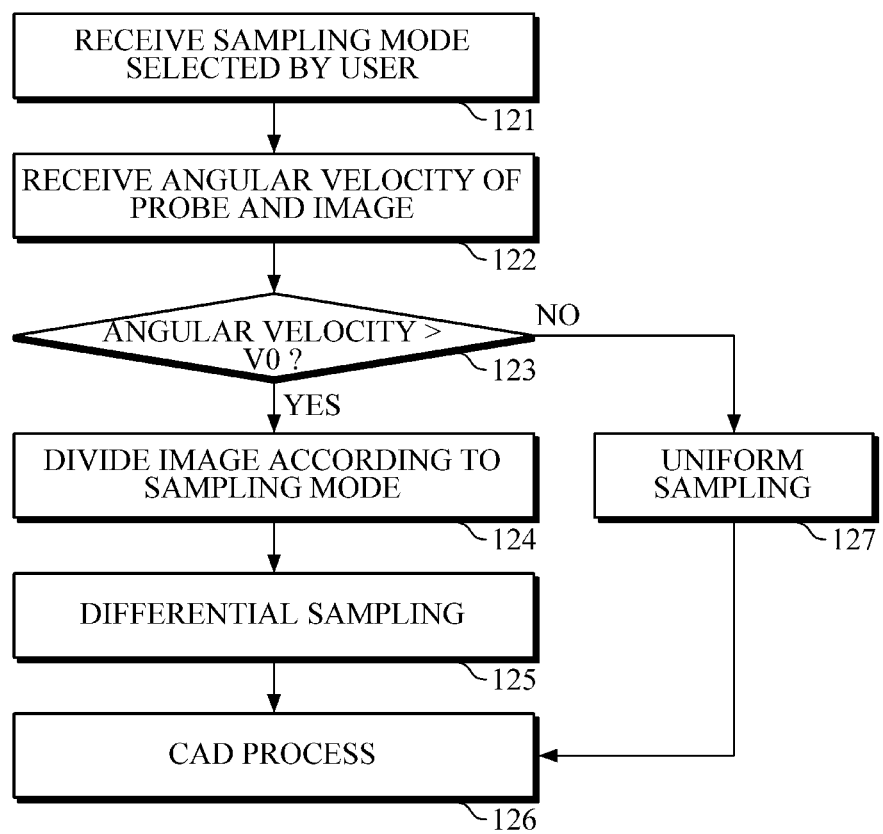
FIG. 12 is a diagram illustrating an example of an image sampling method.

FIG. 12 is a diagram illustrating an example of an image sampling method (120). Referring to FIG. 12, the image sampling method (120) represents a process of dividing a capture image according to a sampling mode selected by a user and a detected probe angular velocity, and performing a differential sampling. The operations in FIG. 12 may be performed in the sequence and manner as shown, although the order of some operations may be changed or some of the operations omitted without departing from the spirit and scope of the illustrative examples described. Many of the operations shown in FIG. 12 may be performed in parallel or concurrently. The above descriptions of FIGS. 1-11, is also applicable to FIG. 12, and is incorporated herein by reference. Thus, the above description may not be repeated here.

According to the image sampling method (120), in 121, a user may select a sampling mode before performing a CAD process on an ultrasound image. In operation 121, for example, a plurality of sampling modes stored in a memory of a computing device are provided to a user through a user interface displayed on a display of the computing device, and one of the plurality of sampling modes is selected by a user through a keyboard/mouse, or other types of input for the computing device.

The plurality of sampling modes may be defined in advance. The sampling modes may be defined in consideration of the position (i.e., a depth) of organs or lesions from a surface of a human body, which are desired by a user for diagnosis, and a detection probability of lesions desired for diagnosis. Accordingly, a user may select a sampling mode that is determined to be suitable based on the position of an organ desired for diagnosis and the detection probability of a lesion desired for diagnosis.

When the sampling mode selected by the user is received, in 122, an angular velocity of a probe capturing an ultrasound image is detected, and a captured image is received. In 123, it is checked whether a magnitude of the detected angular velocity exceeds a predetermined threshold value V0. If the magnitude of the probe angular velocity does not exceed a threshold value (i.e., NO is returned from operation 123), it is regarded that the probe does not change an angle, and in 127 uniform sampling is performed. The result of the uniform sampling is provided to the CAD process 126, and lesion detection is performed.

If the magnitude of the probe angular velocity exceeds a threshold value (i.e., YES is returned from operation 123), it is determined that there is a need to perform sampling in consideration of a change in the probe angle, and thus, in 124, the captured image is divided according to a sampling mode.

In 124, each of the images captured by the probe is divided into a plurality of sub-regions, according to segmentation parameters that are set based on the selected sampling mode. The segmentation parameters correspond to each sampling mode may include a parameter of designating such that an image is designated into a plurality of sub-regions in the depth direction D, a parameter of designating such that an image is divided into a plurality of sub-regions in the depth direction D and the width direction W, a parameter of designating shapes of sub-regions, and a parameter of designating areas of sub regions.

In 125, differential sampling is performed. In 125, with respect to each image, one or more some sub region(s) may be selected. In 126, the selected one or more some sub region(s) may be provided to a CAD process. The criterion for selecting a sub-region may be determined by sampling parameters that are set corresponding to each sampling mode. For example, the sampling parameter may designate a sampling rate of an image based on the depth direction D, and a sampling rate of an image based on the width direction W. As another example, the sampling parameter may designate such that a sub-region of an image located distant in the depth direction D (that is, a lower portion of the image) may be selected at a higher sampling rate when compared to a sub-region located adjacent in the depth direction (that is, an upper portion).

Figure 13:
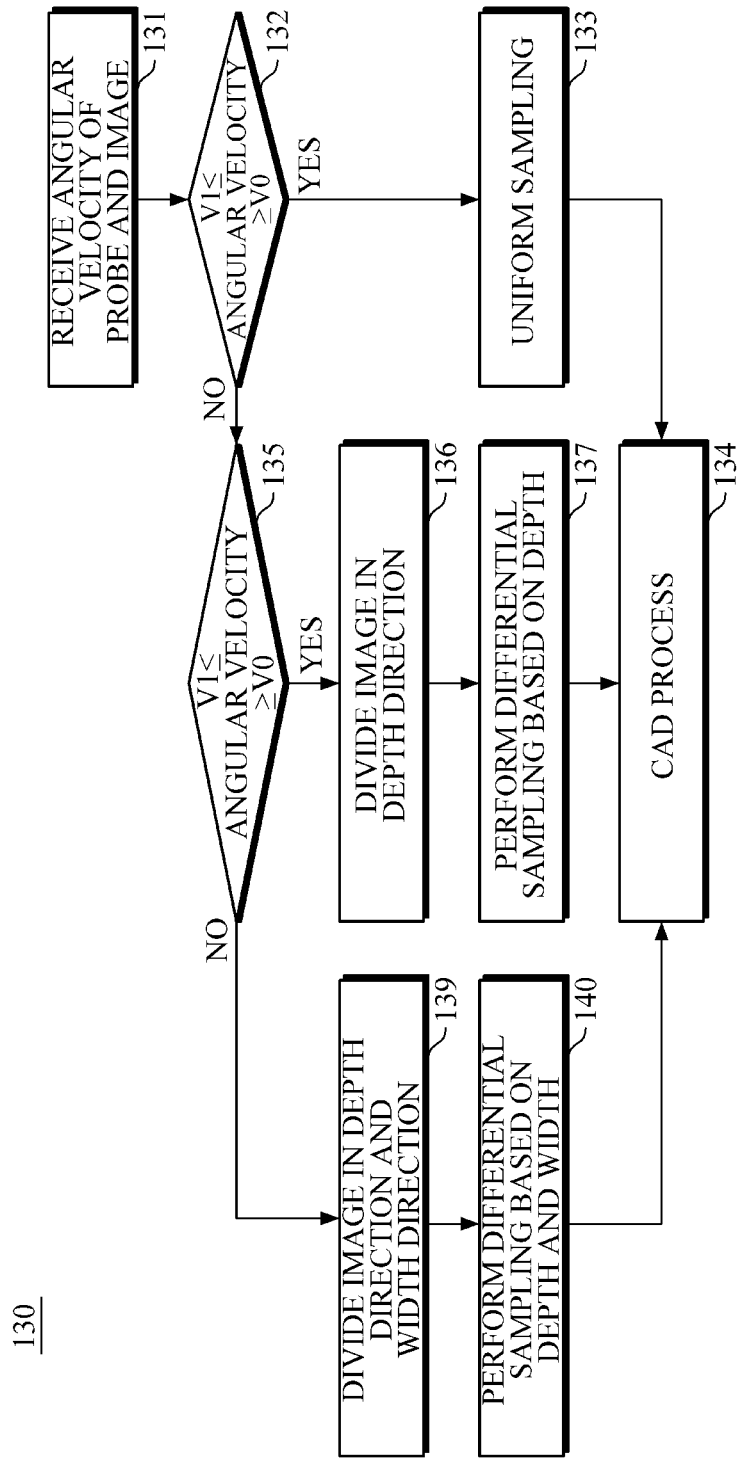
FIG. 13 is a diagram illustrating an example of an image sampling method.

FIG. 13 is a diagram illustrating an example of an image sampling method (130). Referring to FIG. 13, the image sampling method 130 represents a process of dividing a capture image in a depth direction/or a width direction according to a detected probe angular velocity, and performs differential sampling based on depths and/or widths. The operations in FIG. 13 may be performed in the sequence and manner as shown, although the order of some operations may be changed or some of the operations omitted without departing from the spirit and scope of the illustrative examples described. Many of the operations shown in FIG. 13 may be performed in parallel or concurrently. The above descriptions of FIGS. 1-12, is also applicable to FIG. 13, and is incorporated herein by reference. Thus, the above description may not be repeated here.

According to the image sampling method (130), in 131, an angular velocity of a probe capturing an ultrasound image is detected, and a captured image is received. In 132, it is checked whether a magnitude of the detected angular velocity exceeds a predetermined threshold value V0.

If the magnitude of the probe angular velocity does not exceed threshold value (i.e., NO is returned from operation 132), it is determined that there is no need to perform sampling in consideration of a change in the probe angle, and thus, in 133, uniform sampling is performed. In 134, the result of the uniform sampling is transmitted to a CAD process.

If the magnitude of the probe angular velocity exceeds a threshold value (i.e., YES is returned from operation 132), it is determined that there is a need to perform sampling in consideration of a change in the probe angle. In this example, sampling based on the velocity of a change in the probe angle is performed. In 135, the magnitude of an angular velocity is checked to determine whether the magnitude is larger than a predetermined reference value V1 (where V1>V0).

If the magnitude of the probe angular velocity is equal to or smaller than V1, in 136, an image is divided in the depth direction. In 137, differential sampling based on the depth direction is performed. In 134, the result of the differential sampling is provided to the CAD process in a similar manner as the description of FIG. 11.

If the magnitude of the probe angular velocity is larger than V1, in 139, an image is divided in the depth direction and the width direction. In 140, differential sampling based on the depth direction and the width direction is performed.

The result of the differential sampling is provided to the CAD process in 134. The dividing in the width direction and the differential sampling based on the width direction may be performed in a similar manner as those of the depth direction.

Although the magnitude of the probe angular velocity is described as being determined using two values V0 and V1 in FIG. 13, the description is for an illustrative purpose only. The magnitude of the probe angular velocity may be determined in a larger number of operations based on a larger number of criteria without departing from the spirit and scope of the illustrative examples described. In addition, various types of dividing methods and differential sampling rates may be determined based on the respective probe angular velocities without departing from the spirit and scope of the illustrative examples described.

The components of the above-described image sampling apparatus can be implemented by hardware including a circuit configured to perform a particular function. The apparatuses, components, and units described herein may be implemented using hardware components. The hardware components may include, for example, controllers, sensors, processors, generators, drivers, and other equivalent electronic components. The hardware components may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The hardware components may run an operating system (OS) and one or more software applications that run on the OS. The hardware components also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a hardware component may include multiple processors or a processor and a controller. In addition, different processing configurations are possible, such a parallel processors.

The user input device may be a device allowing a user to input a command such that a processor performs a particular task, or allowing a user to input data required for execution of a particular task. The user input device may include physical/virtual keyboards or keypads, key buttons, a mouse, a joystick, a touch-sensitive input device, motion-sensitive input device, or a microphone. The presentation device may include a display, a printer, a speaker or a vibration device.

The sampling mode selector, sampling mode storage, probe angular velocity detector, image segmenter, differential sampler, and CAD processor described herein may be implemented using hardware components, such as, for example a microprocessor. The microprocessor may be a multipurpose, programmable device that accepts digital data as input, processes it according to instructions stored in its memory, and provides results as output, such as, for example, Samsung's Exynos, Qualcomm's Snapdragon, NVIDIA's Tegra, Intel's Itanium, Intel's Xeon, Intel's Core i5, Intel's Core i7, Intel's Core 2, Intel's Pentium III, Intel's Pentium II, Intel's Celeron, Intel's Atom, DEC's Alpha 21064, DEC's Alpha 21164, DEC's Alpha 21264, DEC's Alpha 21364, and DEC's StrongARM.

The processes, functions, and methods described above can be written as a computer program, a piece of code, an instruction, or some combination thereof, for independently or collectively instructing or configuring the processing device to operate as desired. Software and data may be embodied permanently or temporarily in any type of machine, component, physical or virtual equipment, computer storage medium or device that is capable of providing instructions or data to or being interpreted by the processing device. The software also may be distributed over network coupled computer systems so that the software is stored and executed in a distributed fashion. In particular, the software and data may be stored by one or more non-transitory computer readable recording mediums. The non-transitory computer readable recording medium may include any data storage device that can store data that can be thereafter read by a computer system or processing device. Examples of the non-transitory computer readable recording medium include read-only memory (ROM), random-access memory (RAM), Compact Disc Read-only Memory (CD-ROMs), magnetic tapes, USBs, floppy disks, hard disks, optical recording media (e.g., CD-ROMs, or DVDs), and PC interfaces (e.g., PCI, PCI-express, Wi-Fi, etc.). In addition, functional programs, codes, and code segments for accomplishing the example disclosed herein can be construed by programmers skilled in the art based on the flow diagrams and block diagrams of the figures and their corresponding descriptions as provided herein.

The computing device described herein may refer to mobile devices such as, for example, a cellular phone, a smart phone, a wearable smart device (such as, for example, a ring, a watch, a pair of glasses, glasses-type device, a bracelet, an ankle bracket, a belt, a necklace, an earring, a headband, a helmet, a device embedded in the cloths or the like), a personal computer (PC), a tablet personal computer (tablet), a phablet, a mobile internet device (MID), a personal digital assistant (PDA), an enterprise digital assistant (EDA), a digital camera, a digital video camera, a portable game console, an MP3 player, a portable/personal multimedia player (PMP), a handheld e-book, an ultra mobile personal computer (UMPC), a portable lab-top PC, a global positioning system (GPS) navigation, a personal navigation device or portable navigation device (PND), a handheld game console, an e-book, and devices such as a high definition television (HDTV), an optical disc player, a DVD player, a Blue-ray player, a setup box, robot cleaners, or any other device capable of wireless communication or network communication consistent with that disclosed herein. The computing device may be a stand-alone type device, or may include a plurality of computing devices that cooperate with each other through a communication network.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An apparatus for sampling images comprising:
a probe configured to:
capture an image, and
detect an angular velocity of the probe representing a change in an angle of the probe at a surface of an object; and
at least one processor configured to:
receive the angular velocity and the image captured by the probe,
segment the image into sub-regions along a depth direction from the surface to an inside of the object,
sample the sub-regions with a different sampling rate based on a position of each sub-region, and
determine a number of the sub-regions and a sampling rate of the each sub-region based on the angular velocity.

2. The apparatus of claim 1, wherein the at least one processor is further configured to segment the image in a width direction perpendicular to the depth direction.

3. The apparatus of claim 1, wherein at least one of a shape of the sub-regions and a size of the sub-regions are predetermined.

4. The apparatus of claim 1, wherein at least one of a shape of the sub-regions and a size of the sub-regions are determined based on the angular velocity.

5. The apparatus of claim 1, wherein the at least one processor is further configured to:
receive a selection of a sampling mode, and
determine at least one of a shape of the sub-regions, a size of the sub-regions, the number of the sub-regions, and the sampling rate of each sub-region, based on the selected sampling mode and the angular velocity.

6. The apparatus of claim 5,
wherein the sampling mode is selected from sampling modes that are stored in advance, and
wherein each sampling mode of the sampling modes is defined based on a position of a lesion expected to be included in the image and a probability of detecting the lesion.

7. The apparatus of claim 1, wherein the at least one processor is further configured to sample the sub-regions with a higher sampling rate as a depth from the surface of the object increases.

8. The apparatus of claim 1, wherein the object comprises a human body.

9. A computer aided diagnosis (CAD) apparatus comprising:
a probe configured to:
capture an image, and
detect an angular velocity of the probe representing a change in an angle of the probe at a surface of an object; and
at least one processor configured to:
receive the angular velocity and the image captured by the probe,
segment the image into sub-regions along a depth direction from the surface to an inside of the object,
sample the sub-regions with a different sampling rate based on a depth of each sub-region from the surface of the object,
perform image processing to detect a lesion based on a sampling result, and
determine a number of the sub-regions and a sampling rate of the each sub-region based on the angular velocity.

10. The apparatus of claim 9, wherein the at least one processor is further configured to sample the sub-regions with a higher sampling rate as a depth from the surface of the object increases.

11. The apparatus of claim 9,
wherein the probe comprises a sensor, and
wherein the probe is further configured to transmit the angular velocity detected by the sensor to the at least one processor.

12. A method of sampling an image, the method comprising:
detecting an angular velocity of a probe representing a change in an angle of the probe at a surface of an object;
receiving the angular velocity and an image captured by the probe;
segmenting the image into sub-regions along a depth direction from the surface to an inside of the object; and
differentially sampling the sub-regions with a sampling rate that is determined depending on a position of each sub-region,
wherein a number of the sub-regions and a sampling rate of the each sub-region are determined based on the angular velocity.

13. The method of claim 12, wherein the segmenting of the image into the sub-regions further comprises segmenting the image in a width direction perpendicular to the depth direction.

14. The method of claim 12, wherein at least one of a shape of the sub-regions and a size of the sub-regions are predetermined.

15. The method of claim 12, wherein at least one of a shape of the sub-regions and a size of the sub-regions are determined based on the angular velocity.

16. The method of claim 12, further comprising:
receiving a selection of a sampling mode,
wherein a shape of the sub-regions, a size of the sub-regions, and the number of the sub-regions, and a sampling rate of each sub-region, are determined based on the selected sampling mode and the angular velocity.

17. The method of claim 16,
wherein the sampling mode is selected from sampling modes that are stored in advance, and
wherein each sampling mode of the plurality of sampling modes is defined based on a position of a lesion expected to be included in the image and a probability of detecting the lesion.

18. The method of claim 12, wherein the differential sampling of the sub-regions comprises sampling the sub-regions with a higher sampling rate as a depth from the surface of the object increases.

19. A method of sampling an image, the method comprising:
detecting an angular velocity of a probe representing a change in an angle of the probe at a surface of an object;
segmenting an image into sub-regions along a direction perpendicular to the surface of the object, in response to the angular velocity being greater than a first threshold; and
differentially sampling the sub-regions with a sampling rate that is determined based on a position of each sub-region from the surface of the object,
wherein a number of the sub-regions and a sampling rate of the each sub-region are determined based on the angular velocity.

20. The method of claim 19, wherein the differential sampling of the sub-regions comprises differentially sampling the sub-regions based on a selected sampling mode and a depth of the each sub-region from the surface of the object.

21. The method of claim 19, wherein the segmenting of the image into the sub-regions comprises segmenting the image in a depth direction perpendicular to the surface of the object and in a width direction perpendicular to the depth direction, in response to the angular velocity being greater than a second threshold.

* * * * *